United States Patent
Bremer et al.

(10) Patent No.: US 12,312,529 B2
(45) Date of Patent: May 27, 2025

(54) LIQUID CRYSTAL COMPOUNDS

(71) Applicant: MERCK PATENT GMBH, Darmstadt (DE)

(72) Inventors: Matthias Bremer, Darmstadt (DE); Atsutaka Manabe, Darmstadt (DE); Martin Kraska, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 18/039,793

(22) PCT Filed: Nov. 30, 2021

(86) PCT No.: PCT/EP2021/083546
§ 371 (c)(1),
(2) Date: Jun. 1, 2023

(87) PCT Pub. No.: WO2022/117554
PCT Pub. Date: Jun. 9, 2022

(65) Prior Publication Data
US 2024/0043747 A1    Feb. 8, 2024

(30) Foreign Application Priority Data
Dec. 2, 2020 (EP) .................... 20211313

(51) Int. Cl.
G02F 1/1333    (2006.01)
C07C 255/54   (2006.01)
C07C 255/55   (2006.01)
C09K 19/02    (2006.01)
C09K 19/20    (2006.01)
C09K 19/34    (2006.01)
C09K 19/04    (2006.01)

(52) U.S. Cl.
CPC ........ *C09K 19/2007* (2013.01); *C07C 255/54* (2013.01); *C07C 255/55* (2013.01); *C09K 19/0225* (2013.01); *C09K 19/3402* (2013.01); *C09K 2019/0466* (2013.01); *C09K 2019/2042* (2013.01); *C09K 2019/3422* (2013.01)

(58) Field of Classification Search
CPC ............ C09K 19/20; C09K 19/2007; C09K 19/3402; C09K 2019/0466; C09K 2019/2042; C09K 2019/3422; C09K 2019/0444; G02F 1/1333; C07C 255/54; C07C 255/55
See application file for complete search history.

(56) References Cited

U.S. PATENT DOCUMENTS

| | | | |
|---|---|---|---|
| 9,481,828 B2 * | 11/2016 | Yun | C09K 19/44 |
| 9,938,464 B2 | 4/2018 | Wittek et al. | |
| 2018/0237696 A1 | 8/2018 | Tuffin et al. | |
| 2024/0002727 A1 * | 1/2024 | Bremer | C09K 19/0225 |
| 2024/0043747 A1 * | 2/2024 | Bremer | C09K 19/3402 |
| 2024/0052242 A1 * | 2/2024 | Bremer | C09K 19/0225 |

FOREIGN PATENT DOCUMENTS

| | | | | |
|---|---|---|---|---|
| CN | 103333700 A | | 10/2013 | |
| CN | 103351878 A | | 10/2013 | |
| CN | 104560058 A | * | 4/2015 | ............ C09K 19/44 |
| CN | 104650923 A | | 5/2015 | |
| CN | 107922843 A | | 4/2018 | |
| DE | 102007009944 A1 | | 9/2007 | |
| JP | 2016175886 A | | 10/2016 | |
| WO | 2015101405 A1 | | 7/2015 | |

OTHER PUBLICATIONS

H. Nishikawa et al.,"A Fluid Liquid-Crystal Material with Highly Polar Order" Adv. Mater., 2017, 29, 1702354 (pp. 1-8).
N. Sebastián et al., "Ferroelectric-Ferroelastic Phase Transition in a Nematic Liquid Crystal" Physical Review Letters, 2020, 124, 037801-1-037801-6.
X. Chen et al., "First-principles experimental demonstration of ferroelectricity in a thermotropic nematic liquid crystal: Polar domains and striking electro-optics" PNAS Latest Articles, 2020, 117, 25, 14021-14031.
O. D. Lavrentovic, "Ferroelectric nematic liquid crystal, a century in waiting" PNAS, 2020, 117, 26, 14629-14631.
International search report PCT/EP2021/083546 dated Feb. 9, 2022 (pp. 1-3).

* cited by examiner

*Primary Examiner* — Geraldina Visconti
(74) *Attorney, Agent, or Firm* — Millen, White, Zelano & Branigan; Brion P. Heaney

(57) ABSTRACT

New compounds and their mixtures enable the formation of the ferroelectric nematic liquid crystalline phase at ambient temperature. Compounds of the formula I are presented,

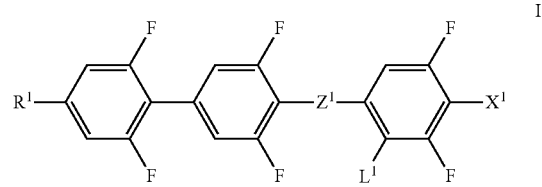

in which the variable groups have the meanings indicated in claim 1. Liquid crystal media comprise at least one compound of the formula I.

23 Claims, No Drawings

LIQUID CRYSTAL COMPOUNDS

An aspect of the invention relates to compounds of the formula I as defined below, which sustain a ferroelectric nematic liquid crystalline phase. In addition, the invention encompasses liquid crystal media comprising at least one compound of the formula I, and the use thereof as component(s) in liquid crystal media. In addition, the present invention relates to liquid crystal displays and electro-optical elements which contain the liquid crystal compounds and media according to the invention.

In previous years, the areas of application for liquid crystal compounds have been considerably expanded to various types of display devices, electro-optical devices, electronic components, sensors, etc. For this reason, a number of different structures have been proposed, in particular in the area of nematic liquid crystals. The nematic liquid-crystal mixtures have to date found the broadest use in flat-panel display devices. They have been employed, in particular, in passive TN or STN matrix displays or systems having a TFT active matrix, including the well-known TN, IPS, FFS and VA systems.

Most of these devices employ the nematic liquid crystal phase, including all common LCD television sets, LCD desktop monitors and mobile LCD devices. Some alternative liquid crystalline phases are known, like ferroelectric smectic or blue phase. However, a ferroelectric nematic phase ($N_f$-LC phase) was only postulated by theory for decades, without finding a suitable liquid crystalline material with such property. Only recently, two chemical structures were proposed to have ferroelectric nematic behaviour.

Hiroya Nishikawa, Kazuya Shiroshita, Hiroki Higuchi, Yasushi Okumura, Yasuhiro Haseba, Shin-ichi Yamamoto, Koki Sago, and Hirotsugu Kikuchi, *Adv. Mater.* 2017, 29, 1702354, describe a compound of formula A to have a ferroelectric nematic behaviour at temperatures between about 45° C. to 68° C.

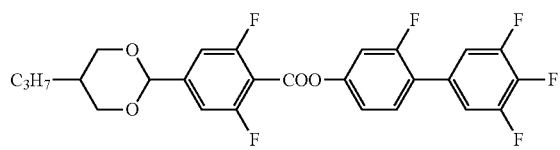

A

Further, Nerea Sebastián, Luka Cmok, Richard J. Mandle, Maria Rosario de la Fuente, Irena Drevenšek Olenik, Martin Čopič and Alenka Mertelj, Physical Review Letters (2020) 124, 037801 describe a compound of formula B with similar behaviour between about 120° C. to 133° C.

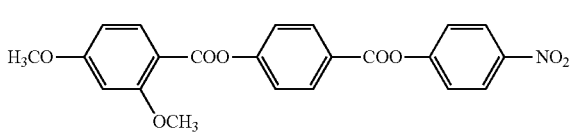

B

Further comparison of the two only available substances for $N_f$-LC phases is presented by Xi CHen et al., PNAS Jun. 23, 2020 117 (25) 14021-14031. The high significance of the advent of the new $N_f$-LC phase underlines 0. D. Lavrentovic, ProcNatAcadSciUSA (2020), 117(26), 14629-14631.

So far no liquid crystalline compound was described having a ferroelectric nematic liquid crystalline phase ($N_f$-LC phase) close to room temperature. Exploitation of the $N_f$-LC phase for technical applications would clearly benefit from applicability to ambient temperatures. Display applications are usually designed to have a working range above and below room temperature, e. g. 0 to 50° C. and preferably more.

A ferroelectric nematic display is proposed in DE19629551 A1, however it is silent about the materials that can fulfil the requested ferroelectric nematic properties.

The use of fluorinated liquid crystal substances is known to the person skilled in the art. Various compounds containing two 2,6-difluorinated 1,4-phenylene rings have already been described as liquid-crystalline or mesogenic material, such as, for example, in the publication WO 2015/101405 A1 and various more. The compounds proposed therein do not contain three 2,6-difluorinated phenylene rings and a bridging group C(O)O or $CF_2O$ in the same pattern, nor are they reported to have any ferroelectric properties.

An object of the present invention was finding novel stable compounds which are suitable as single compounds or component(s) of ferroelectric nematic liquid crystal media ($N_f$-LC phase media). In particular, the compounds should simultaneously have a $N_f$-LC phase or support such phase in a $N_f$-LC medium. They should also have a moderate to high optical anisotropy for achieving the electrooptical switching effect as with conventional nematic LC media.

In view of the very wide variety of areas of application of compounds of this type having high Δε, it was desirable to have available further compounds, preferably having a high clearing point and low melting point, while showing a broad and suitable temperature range of the ferroelectric nematic phase.

It was thus a further object of the invention to find novel stable compounds which are suitable as component(s) of ferroelectric nematic liquid crystal media, in particular for displays analogous to conventional nematic TN, STN, IPS, FFS and TN-TFT displays.

In addition, it was an aim for the compounds according to the invention to be thermally and photochemically stable under the conditions prevailing in the areas of application. As mesogens, they should facilitate a broad mesogenic phase in mixtures with liquid crystal co-components and be readily miscible with mesogenic base mixtures, in particular at room temperature or lower.

Surprisingly, it has been found that the compounds according to the invention are eminently suitable as components of $N_f$-LC media. The ferroelectric nematic phase can be achieved at an advantageous temperature range, at or close to ambient temperatures. The repository of compounds showing the hitherto very unusual ferroelectric nematic phase is considerable broadened. They can be used to obtain liquid crystal media for displays which require particularly high or even extremely high dielectric anisotropies, in particular for IPS or FFS displays, but also for TN or STN displays. The compounds according to the invention are sufficiently stable and colourless. In particular, they are distinguished by extraordinarily high dielectric anisotropies (Δε), owing to which much lower threshold voltages are necessary on use in optical switching elements. They have reasonably good solubility for compounds having comparable properties and can be admixed with similar compounds almost unlimited. In addition, the compounds according to the invention have a high clearing point. The compounds have low melting points or can be stably kept below their melting point as super-cooled melts, which enables the formation of the desired $N_F$-LC phase already at room temperature and below.

The provision of the compounds according to the invention very generally considerably broadens the range of liquid crystal substances that are suitable, from various applicational points of view, for the preparation of ferroelectric nematic liquid crystal mixtures.

The compounds according to the invention have a broad range of applications. Depending on the choice of substituents, these compounds can serve as base materials of which liquid crystal media are predominantly composed. However, it is also possible to add liquid-crystalline base materials from other classes of compound to the compounds of the formula I according to the invention in order, for example, to further lower the melting points, to influence the dielectric and/or optical anisotropy of a dielectric of this type and/or to optimise its threshold voltage and/or its viscosity.

The use of the compounds of the invention enables LC media having extremely short response times compared with conventional nematic LC systems as currently used in standard displays. The invention may as such improve substantially the means for displaying moving images. The high dielectric constant is also interesting for dielectrics in capacitors.

The liquid crystal compounds according to the invention can be used as component(s) of liquid crystal media, in particular for displays based on the principle of the twisted cell, the guest-host effect, the effect of deformation of aligned phases DAP or ECB (electrically controlled birefringence), the IPS (in-plane switching) effect or the effect of dynamic scattering.

The invention thus relates to compounds of the formula I,

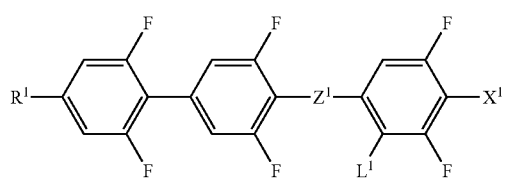

I in which
$X^1$ is CN, F, $CF_3$, $OCF_3$, SCN, NCS, $SF_5$ or O—CF=$CF_2$,
$Z^1$ is —C(O)O— or —$CF_2$O—, and
$L^1$ H or $CH_3$, preferably H,
$R^1$ denotes an alkyl radical having 1 to 15 C atoms, where, in addition, one or more $CH_2$ groups in these radicals, including any terminal carbon, may in each case be replaced, independently of one another, by —C≡C—, —$CF_2$O—, —$OCF_2$—, —CH=CH—,

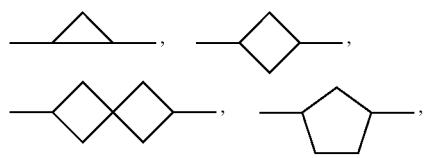

—O—, —S—, —CO—O— or —O—CO— in such a way that O/S atoms are not linked directly to one another, and in which, in addition, one or more H atoms may be replaced by halogen, or denotes H, preferably $R^1$ is a halogenated or unsubstituted alkyl radical having 1 to 15 C atoms, where, in addition, one or more $CH_2$ groups in these radicals may in each case be replaced, independently of one another, by —C≡C— or —CH=CH—.

The invention furthermore relates to the use of the compounds of the formula I in liquid crystal media.

The present invention likewise relates to liquid crystal media which comprise at least one compound of the formula I, preferably two, three, four or more, and optionally any additives.

In the pure state, the compounds of the formula I are colourless and, per se or in mixtures, form liquid-crystalline mesophases in a temperature range which is favourably located for electro-optical use. The compounds according to the invention also support nematic phase ranges outside the range of the $N_F$-phases. In liquid crystal mixtures, the substances according to the invention significantly increase the optical anisotropy. At the same time, the compounds are distinguished by good UV stability.

The radical $R^1$ in the formula I and sub-formulae thereof preferably denotes alkyl having 1 to 8 carbon atoms, alkoxy having 1 to 8 carbon atoms or alkenyl having 2 to 8 carbon atoms. The alkyl chain is preferably linear or it is branched by a single methyl or ethyl substituent, preferably in 2- or 3-position. $R^1$ particularly preferably denotes a straight-chain alkyl radical having 1 to 7 C atoms or an unbranched alkenyl radical having 2 to 8 C atoms, in particular unbranched alkyl having 1 to 5 C atoms.

Alternative preferred radicals $R^1$ are selected from cyclopentyl, 2-fluoroethyl, cyclopropylmethyl, cyclopentylmethyl, cyclopentylmethoxy, cyclobutylmethyl, 2-methylcyclopropyl, 2-methylcyclobutyl, 2-methylbutyl, 2-ethylpentyl and 2-alkyloxyethoxy.

The radical $X^1$ of the formula I preferably denotes CN, F or $CF_3$, more preferably CN or F, and most preferably CN.

Compounds of the formula I containing branched or substituted wing groups $R^1$ may occasionally be of importance owing to better solubility in the conventional liquid-crystalline base materials. The group $R^1$ is preferably straight (not branched) chain.

The radical $R^1$ is particularly preferably selected from the moieties:
H
$CH_3$
$C_2H_5$
n-$C_3H_7$
n-$C_4H_9$
n-$C_5H_{11}$
$C_2H_5CH(CH_3)CH_2$
n-$C_6H_{13}$
n-$C_7H_{15}$
n-$C_3H_7CH(C_2H_5)CH_2$
n-$C_8H_{17}$
c-$C_3H_5$
c-$C_3H_5CH_2$
c-$C_4H_7$
c-$C_5H_7$
c-$C_5H_9$
c-$C_5H_9CH_2$
$CH_2$=CH
$CH_3CH$=CH
$CH_2$=CH($CH_2$)$_2$
$CH_3$O
$C_2H_5$O
n-$C_3H_7$O
n-$C_4H_9$O and
n-C$_5$H$_{11}$O
wherein above and below the following abbreviations for the end groups are used:
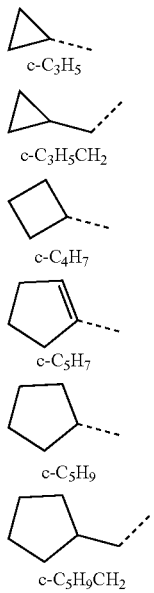
Particularly preferred compounds of the formula I are the compounds of the formulae I-1 to I-20:
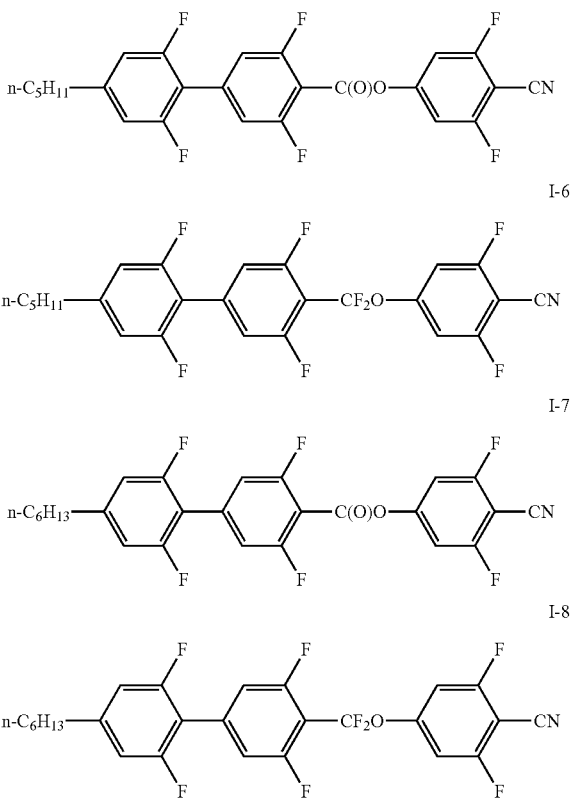
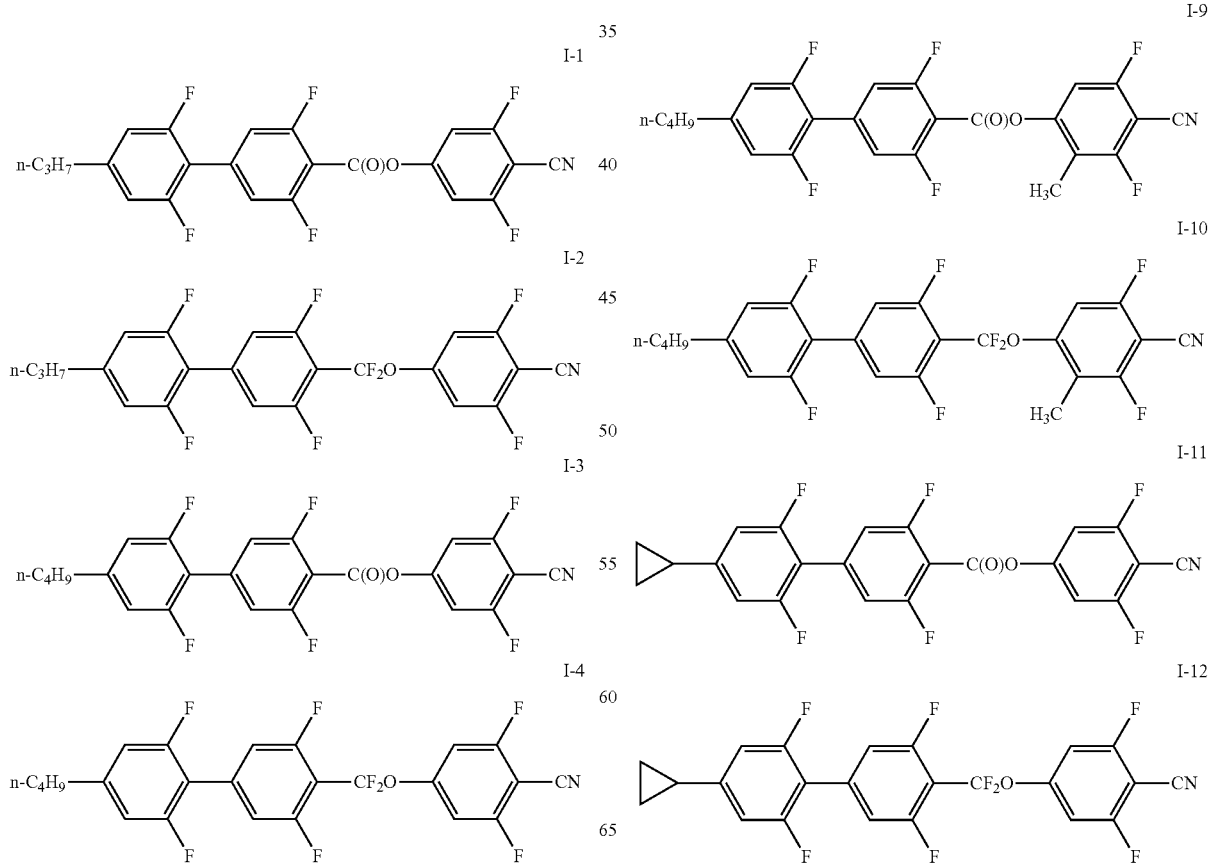

-continued

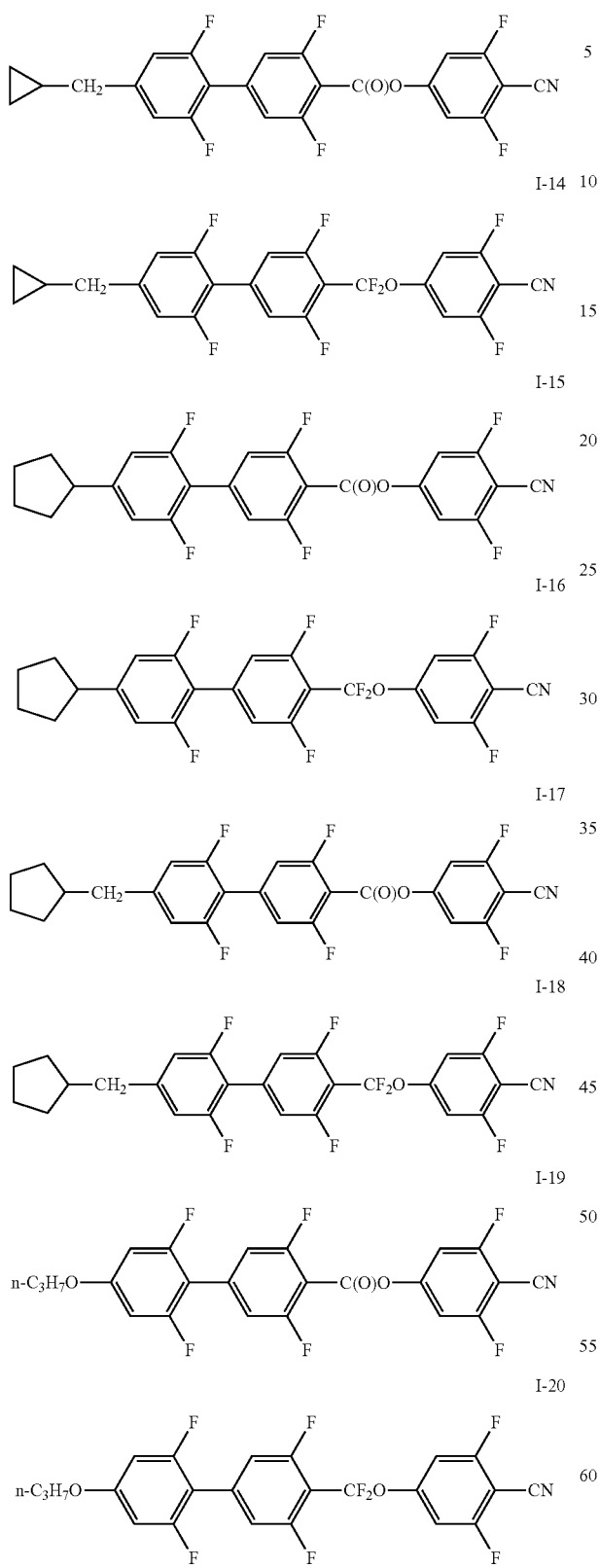

Particularly preferred compounds are of the following formulae:

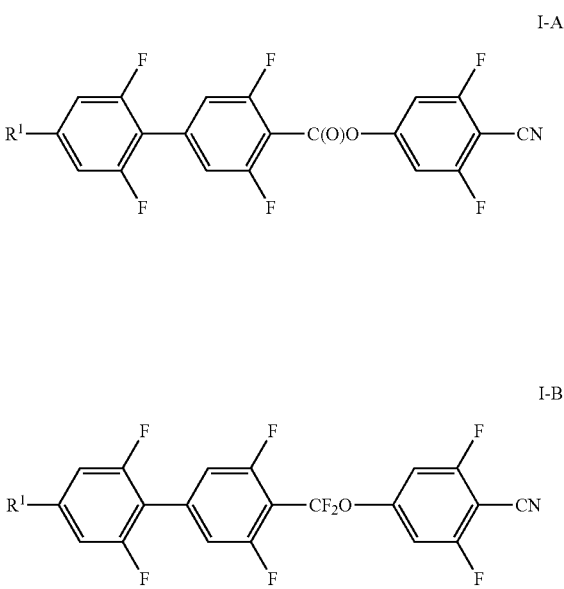

wherein $R^1$ is defined as for formula I or according to the closer specified definitions thereof.

The compounds of the formula I can be prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se, which are not mentioned here in greater detail.

Compounds of the formula I can advantageously be prepared as shown in the following illustrative synthesis and the examples (schemes 1 to 2):

Scheme 1.

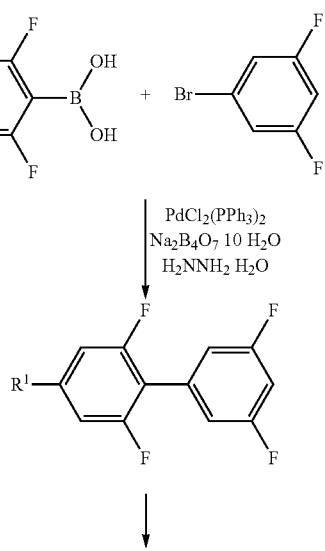

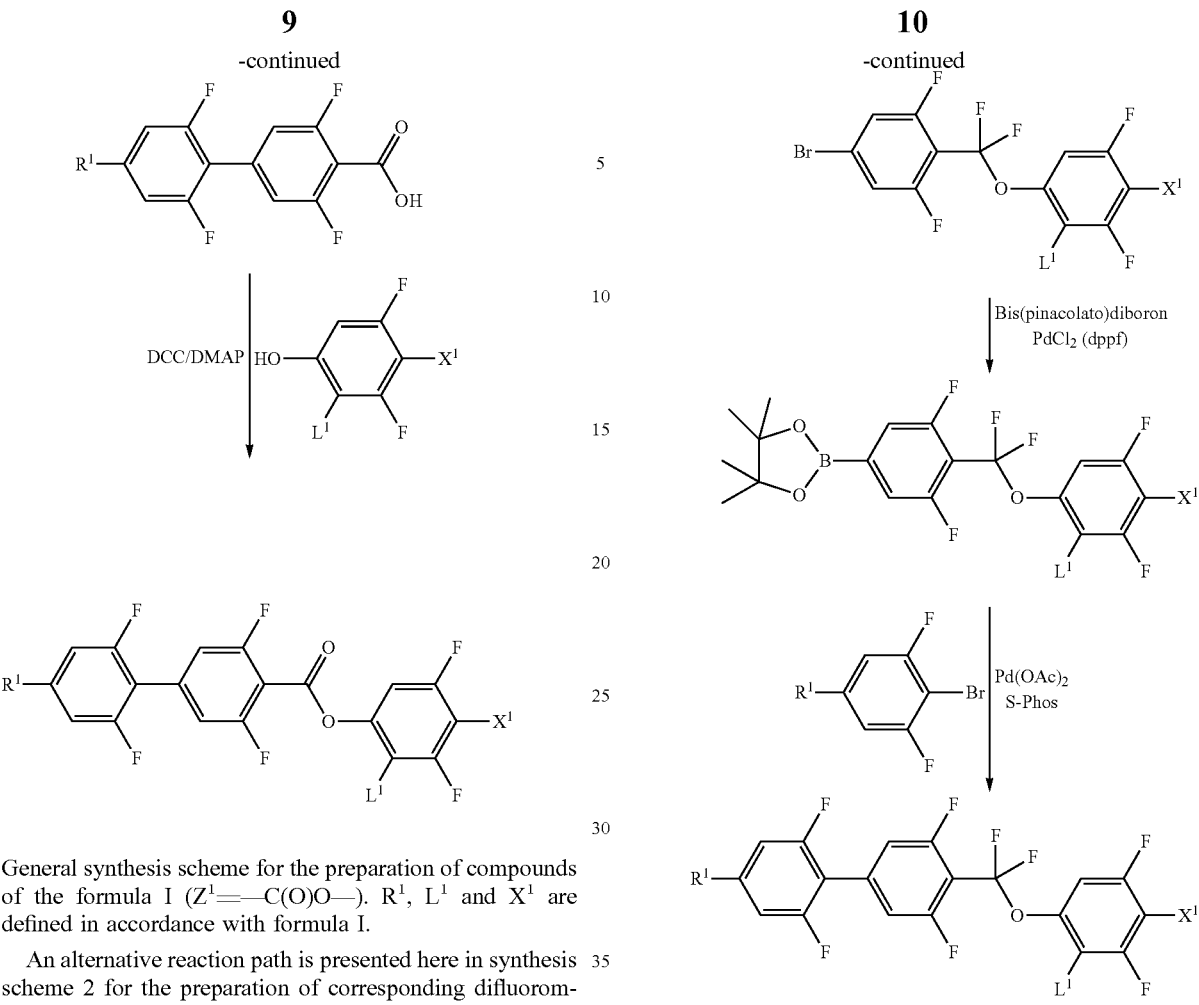

General synthesis scheme for the preparation of compounds of the formula I ($Z^1$=—C(O)O—). $R^1$, $L^1$ and $X^1$ are defined in accordance with formula I.

An alternative reaction path is presented here in synthesis scheme 2 for the preparation of corresponding difluoromethyloxy compounds.

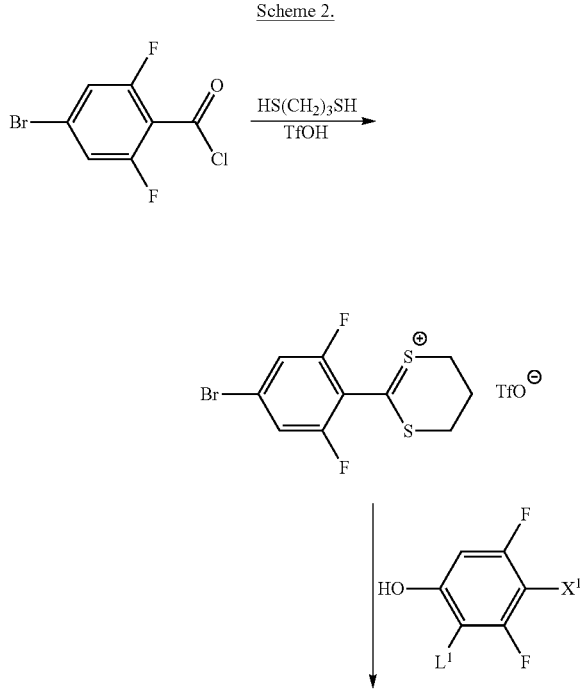

General synthesis scheme for the preparation of compounds of the formula I in which $Z^1$=—$CF_2O$—. $R^1$, $L^1$ and $X^1$ are defined in accordance with formula I.

Corresponding starting materials can generally readily be prepared by the person skilled in the art by synthetic methods known from the literature or are commercially available.

The reaction methods and reagents used are in principle known from the literature. Further reaction conditions are exemplified by the working examples. Further preferred process variants, not mentioned above, are revealed by the examples.

The process and the subsequent work-up of the reaction mixtures obtained by the above processes can basically be carried out as a batch reaction or in a continuous reaction procedure. The continuous reaction procedure encompasses, for example, reaction in a continuous stirred-tank reactor, a stirred-tank reactor cascade, a loop or cross-flow reactor, a flow tube or in a microreactor. The reaction mixtures are optionally worked up, as necessary, by filtration through solid phases, chromatography, separation between immiscible phases (for example extraction), adsorption onto solid supports, removal of solvents and/or azeotropic mixtures by distillation, selective distillation, sublimation, crystallisation, co-crystallisation or by nanofiltration on membranes.

The invention also relates to liquid crystal media comprising one or more of the compounds of the formula I according to the invention. The liquid crystal media preferably comprise at least two components, preferably each one having a ferroelectric nematic phase itself. They are preferably obtained by mixing the components with one another, preferably with heating above the melting point of one or more of the compounds.

A process according to the invention for the preparation of a liquid crystal medium is therefore characterised in that at least one compound of the formula I is mixed with at least one further, preferably mesogenic, more preferably ferroelectric nematic, compound, and additives are optionally added. A preferred process for the preparation of a liquid crystal medium comprises that at least two or more of compounds of formula I as defined herein are mixed, while other compounds and additives are optionally added before or after.

The achievable combinations of temperature range of the ferroelectric nematic phase, clearing point, dielectric anisotropy and response time for liquid crystal media containing the compounds of formula I are far superior to previous materials of such kind from the prior art. Previously only single compound materials were available with limited choice, which all do not have a ferroelectric nematic phase range over suitable temperatures. The LC media according to the invention show ferroelectric-nematic phase over a wide temperature range and which is located in the technical most interesting range around 20° C., i. e. ambient temperature of about 0° to 50° C.

A liquid crystal medium according to the invention may preferably comprise 2, 3, 4 or more compounds of formula I. It was found that a mixture of homologs varying in the nature of the group $R^1$ is still able to support the ferroelectric nematic order of the phase, and even extends the temperature ranges at both ends, at lower temperatures and at higher temperatures. In prior art such mixtures of several mesogenic compounds usually provided only extended nematic or smectic phases. In one preferred embodiment, the liquid crystal medium comprises two, three or more of the compounds of the formula I. With several of the compounds of formula I combined, it is possible to lower the melting point and broaden the $N_f$ phase range of the resulting LC medium.

Further investigations based on these findings reveal that even more compounds exist which support the ferroelectric nematic phase. These are preferably selected from ones which have a ferroelectric nematic phase or which are supporting such a phase in mixtures with the compounds of formula I and with each other. In this embodiment the compounds of the invention are mixed with these further compounds in order to obtain alternative liquid crystal media. Preferably the liquid crystal medium still comprises at least 5% by weight of one or more compounds of formula I, at least 10%, at least 20%, more preferably 40% or more, and most preferably 55% or more.

The liquid crystal media according to the invention may preferably comprise 1 to 40, particularly preferably 4 to 20, components as further constituents besides one or more compounds according to the invention. In particular, these media may comprise 1 to 10 components besides one or more compounds according to the invention. These further constituents are preferably selected from ferroelectric nematic or nematogenic (monotropic or isotropic) substances, as follows.

Prior art ferroelectric substances and similar compounds with high dielectric anisotropy for combination with the current substances are selected from e.g. the following structures:

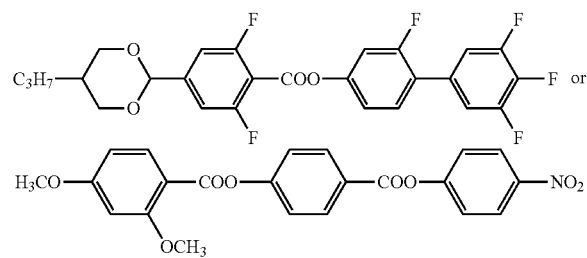

more generally a compound of formula II

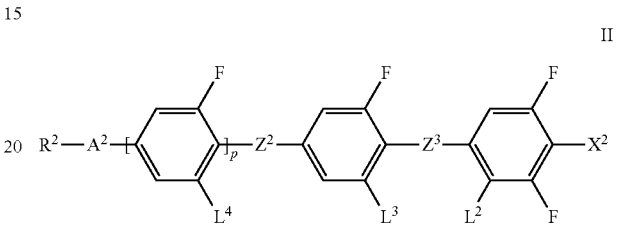

wherein $R^2$ is an alkyl radical having 1 to 15 C atoms, where, in addition, one or more $CH_2$ groups in these radicals, including any terminal carbon, may in each case be replaced, independently of one another, by —C≡C—, —$CF_2O$—, —$OCF_2$—, —CH=CH—,

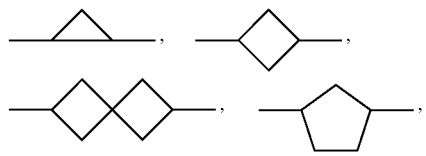

O—, —O—, —S—, —CO—O— or —O—CO— in such a way that O/S atoms are not linked directly to one another, and in which, in addition, one or more H atoms may be replaced by halogen, or denotes H, $Z^2$, $Z^3$ each independently are, a single bond, —C(O)O— or —$CF_2O$—, where preferably one of $Z^2$ and $Z^3$ is a single bond, $L^2$ H or $CH_3$, $L^3$, $L^4$ independently are F or H, preferably F, $X^2$ is CN, F, $CF_3$, $OCF_3$ or SCN, preferably F or CN, $A^2$ is

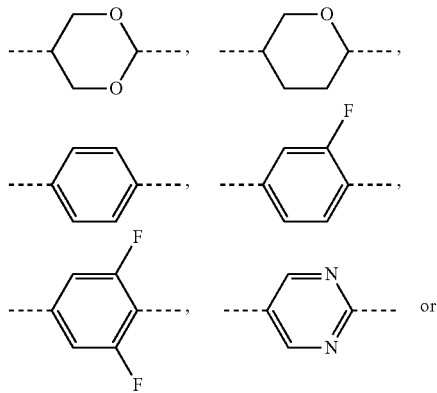

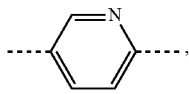

p 0 or 1, and wherein compounds of formula I are excluded from the compounds of formula II.

Exemplary, preferred compounds of formula II

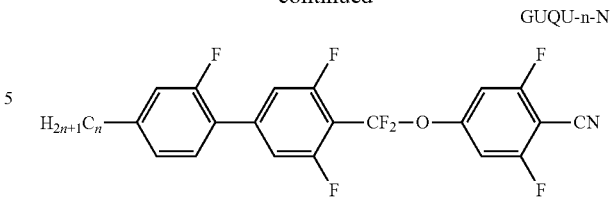

wherein n, is 0, 1, 2, 3, 4, 5, 6, 7 etc.

The media according to the invention preferably comprise 1 to 100%, more preferably 10 to 100%, more preferably 20%, 30%, 40%, 50%, 60%, 70% or more of the compounds of formula I according to the invention.

The liquid-crystal mixtures according to the invention are prepared in a manner which is conventional per se. In general, the desired amount of the components used in lesser amount is dissolved in the components making up the principal constituent, preferably at elevated temperature. It is also possible to mix solutions of the components in an organic solvent, for example in acetone, chloroform or methanol, and to remove the solvent again, for example by distillation, after thorough mixing. It is furthermore possible to prepare the mixtures in other conventional manners, for example by using premixes, for example homologue mixtures, or using so-called "multibottle" systems.

The liquid-crystal mixtures may also comprise further additives known to the person skilled in the art and described in the literature. For example, 0 to 15%, preferably 0 to 10%, of pleochroic dyes, chiral dopants, stabilisers or nanoparticles can be added. The individual compounds added are employed in concentrations of 0.01 to 6%, preferably 0.1 to 3%. However, the concentration data of the other constituents of the liquid-crystal mixtures, i.e. the liquid-crystalline or mesogenic compounds, are given here without taking into account the concentration of these additives. The liquid-crystal mixtures according to the invention enable a significant broadening of the available parameter latitude.

The invention also relates to electro-optical displays (in particular TFT displays having two plane-parallel outer plates, which, together with a frame, form a cell, integrated non-linear elements for switching individual pixels on the outer plates, and a nematic liquid-crystal mixture having positive dielectric anisotropy and high specific resistance located in the cell) which contain media of this type, and to the use of these media for electro-optical purposes.

The expression "alkyl" encompasses unbranched and branched alkyl groups having 1-15 carbon atoms, in particular and preferably the unbranched groups methyl, ethyl, n-propyl, n-butyl, n-pentyl, n-hexyl and n-heptyl and further the groups n-butyl, n-pentyl, n-hexyl substituted by one methyl, ethyl or propyl. Groups having 2-5 carbon atoms are generally preferred.

The expression "alkenyl" encompasses unbranched and branched alkenyl groups having up to 15 carbon atoms, in particular the unbranched groups. Particularly preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having 2 to 5 carbon atoms are generally preferred.

The expression "halogenated alkyl radical" preferably encompasses mono- or polyfluorinated and/or -chlorinated radicals. Perhalogenated radicals are included. Particular preference is given to fluorinated alkyl radicals, in particular $CF_3$, $CH_2CF_3$, $CH_2CHF_2$, $CHF_2$, $CH_2F$, $CHFCF_3$ and $CF_2CHFCF_3$. The expression "halogenated alkenyl radical" and related expressions are explained correspondingly.

The total amount of compounds of the formula I in the mixtures according to the invention is not crucial. The mixtures may therefore comprise one or more further components for the purposes of optimisation of various properties.

The construction of a matrix display according to the invention from polarisers, electrode base plates and surface-treated electrodes corresponds to the usual design for displays of this type. The term usual design is broadly drawn here and also encompasses all derivatives and modifications of the matrix display, in particular also matrix display elements based on poly-Si TFTs.

An essential difference between the displays according to the invention and the hitherto conventional ones based on the twisted nematic cell consists, however, in the choice of the liquid-crystal parameters of the liquid-crystal layer.

The following examples explain the invention without intending to restrict it. The person skilled in the art will be able to glean from the examples working details that are not given in detail in the general description, generalise them in accordance with general expert knowledge and apply them to a specific problem.

Above and below, percentage data denote percent by weight. All temperatures are indicated in degrees Celsius. Furthermore, C=crystalline state, N=nematic phase, Sm=smectic phase (more especially SmA, SmB, etc.), Tg=glass-transition temperature and I=isotropic phase. The data between these symbols represent the transition temperatures. Δn denotes optical anisotropy (589 nm, 20° C.), Δε the dielectric anisotropy (1 kHz, 20° C.).

The physical, physicochemical and electro-optical parameters are determined by generally known methods, as described, inter alia, in the brochure "Merck Liquid Crystals—Licristal®—Physical Properties of Liquid Crystals—Description of the Measurement Methods", 1998, Merck KGaA, Darmstadt.

The occurrence of the ferroelectric nematic phase of the materials is identified using differential scanning calorimetry (DSC), via observation of the textures under a polarising microscope equipped with a hot-stage for controlled cooling resp. heating and additionally confirmed by temperature dependent determination of the dielectric properties.

The conventional dielectric anisotropy Δε of the individual substances is determined at 20° C. and 1 kHz. To this end, 5-10% by weight of the substance to be investigated are measured dissolved in the dielectrically positive mixture ZLI-4792 (Merck KGaA), and the measurement value is extrapolated to a concentration of 100%. The optical anisotropy Δn is determined at 20° C. and a wavelength of 589.3 nm, the rotational viscosity $\gamma_1$ at 20° C., both likewise by linear extrapolation.

The dielectric permittivity of the pure compound is directly determined by measuring the capacitance of at least one test cell containing the compound and having cell thickness of 25 μm with homeotropic and with homogeneous alignment, respectively. Temperature is controlled by a Novocontrol Novocool system set to temperature gradients of +/−1 K/min; +/−2 K/min; +/−5 K/min; +/−10 K/min applied to the sample cell. Capacitance is measured by a Novocontrol alpha-N analyzer at a frequency of 1 kHz with a typical voltage <50 mV down to 0.1 mV in order make sure to be below the threshold of the investigated compound. Measurements are performed both upon heating and upon cooling of the sample(s).

In the present application, unless expressly indicated otherwise, the plural form of a term denotes both the singular form and the plural form, and vice versa. Further combinations of the embodiments and variants of the invention in accordance with the description also arise from the appended claims or from combinations of a plurality of these claims.

EXAMPLES

The present invention is described in detail by the following non-restrictive examples.

Example 1: Synthesis of UUQU-4-N

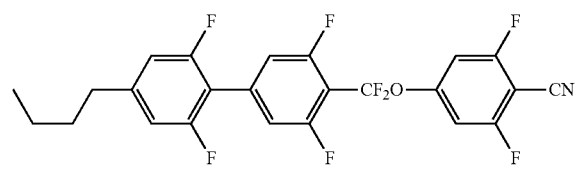

Step 1.1

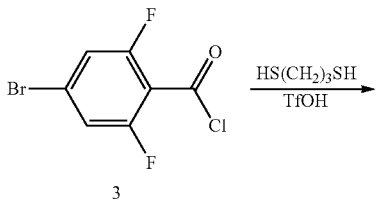

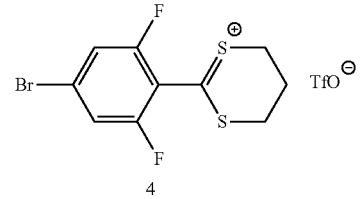

20.3 ml (203 mmol) 1,3-propanedithiol was dissolved in 25.9 ml of toluene and warmed to 80° C. A solution of 34.5 g (135.1 mmol) 3, 0.2 ml trifluoromethanesulfonic acid and 40 ml toluene was prepared and added dropwise to the dithiol solution at 80° C. After the addition was complete the mixture was stirred at 80° C. for 45 min, and then cooled to 20° C. 17.7 ml (200 mmol) trifluoromethanesulfonic acid was added dropwise during a period of 80 min keeping the temperature below 25° C. The toluene was distilled off at 80° C. and 40 mbar, 25 ml of additional toluene was added, and all volatiles were distilled off again. The crystalline residue was used for the next step without further purification.

Step 1.2

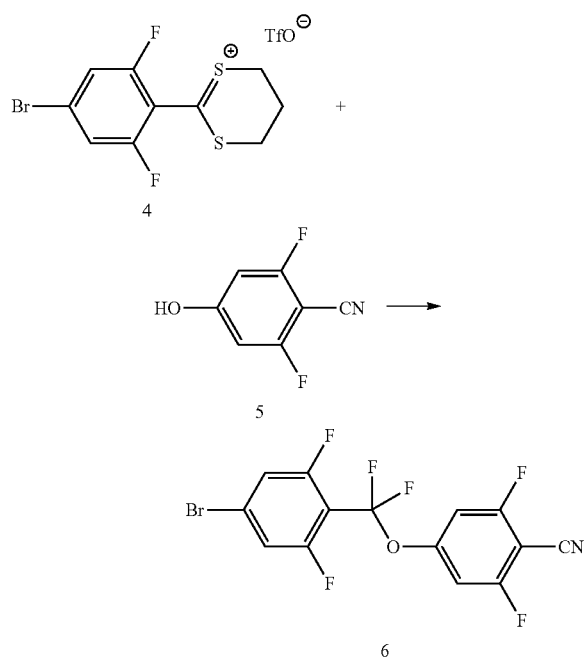

93.1 g (0.6 mol) 5 was suspended in 1.6 L dichloromethane and cooled to 6° C. 83.2 ml (0.6 mol) triethylamine was added dropwise at 5° C., followed by 230 g (0.5 mol) of salt 4. The mixture was stirred at 5° C. for 30 min, then cooled to −75° C. and 244.3 ml (1.5 mol) triethylamine trihydrofluoride was added dropwise. The solution was stirred for one hour at −75° C., and 128 ml (2.5 mol) of bromine dissolved in 400 ml dichloromethane was added. The mixture was stirred for 1.5 h at −70° C. and allowed to warm to 0° C. After the usual workup 132 g (62%) of 6 was obtained as slightly beige crystals.

Step 1.3

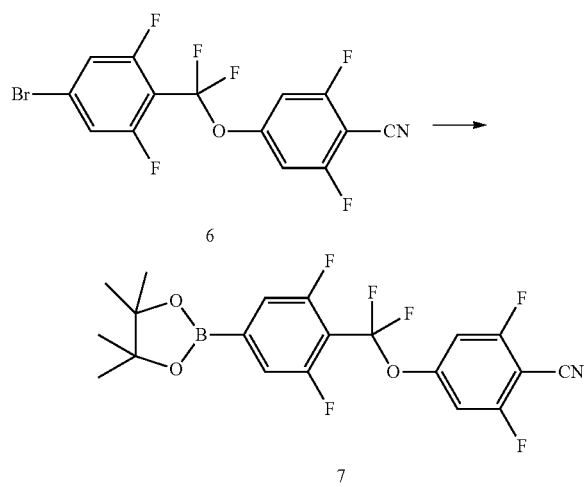

13.8 g (35 mmol) 6 was dissolved in 150 ml 1,4-dioxane, 1.0 g (1.4 mmol) palladium acetate, 10.4 g (0.1 mol) potassium acetate and 13.9 g (53 mmol) bis(pinacolato) boron were added. The mixture was heated under reflux overnight. After the usual workup 12.4 g (80%) of 7 was obtained as slightly yellow crystals.

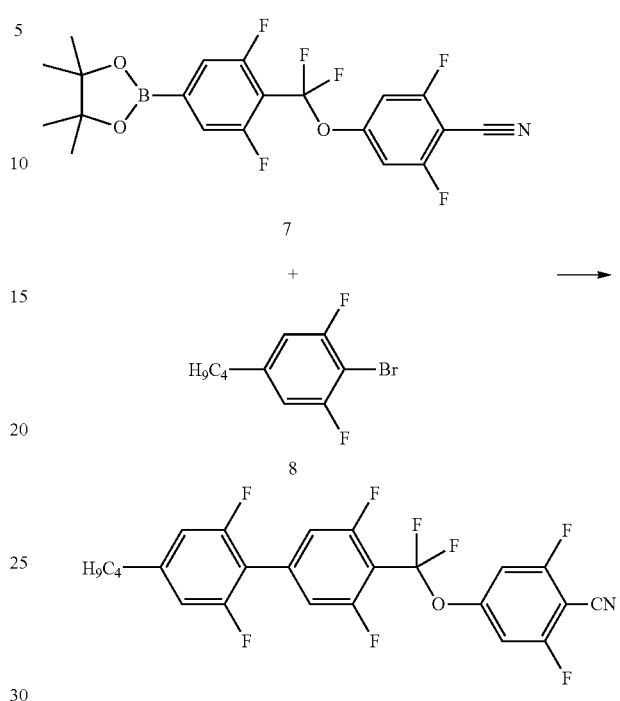

Step 1.4

5.4 g (23 mmol) potassium phosphate was dissolved in 10 ml water. 80 ml of toluene, 2.8 g (11.4 mmol) 1-bromo-2, 6-difluoro-4-butyl benzene 8, 6.3 g (14.2 mmol) 7, 42.2 mg (0.2 mmol) palladium acetate and 126.7 mg (0.3 mmol) S-Phos (2-dicyclohexylphosphino-2',6'-dimethoxybiphenyl) were added and the mixture was heated under reflux overnight. After the usual workup 3.42 g (62%) 9 (UUQU-4-N) was obtained as colorless crystals.

$^{1}$H NMR (400 MHz, Chloroform-d) b 7.16 (d, J=11.0 Hz, 2H), 7.07-6.99 (m, 2H), 6.91-6.81 (m, 2H), 2.69-2.61 (m, 2H), 1.69-1.57 (m, 2H), 1.39 (h, J=7.4 Hz, 2H), 0.96 (t, J=7.3 Hz, 3H).

Melting point: 44° C.
Clearing point: 21° C.
Δn (20° C.)=0.12
Characterization of ferroelectric-nematic behaviour:
C 44 N$_f$ (21.4) I
The dielectric properties are also determined.

TABLE

| Measurement of ε at different temperatures (cooling 1°/min, flat metal electrodes) | | |
|---|---|---|
| T/° C. | ε (1 kHz, T) | Remark |
| 5.0 | 2.34 | crystalline on cooling down |
| 7.0 | 7,730 | |
| 10.0 | 11,300 | |
| 12.0 | 13,800 | |
| 14.0 | 16,500 | |
| 16.0 | 19,100 | |
| 18.0 | 21,500 | |
| 19.8 | 23,100 | ε$_{max}$. |
| 20.0 | 22,800 | |

TABLE-continued

Measurement of ε at different temperatures
(cooling 1°/min, flat metal electrodes)

| T/° C. | ε (1 kHz, T) | Remark |
|---|---|---|
| 20.5 | 2.39 | transition $N_f$- isotropic |
| 21.0 | 2.39 | |
| 22.0 | 2.40 | |

Example 2: Synthesis of UUZU-4-N

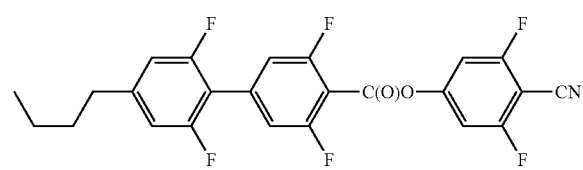

Step 2.1

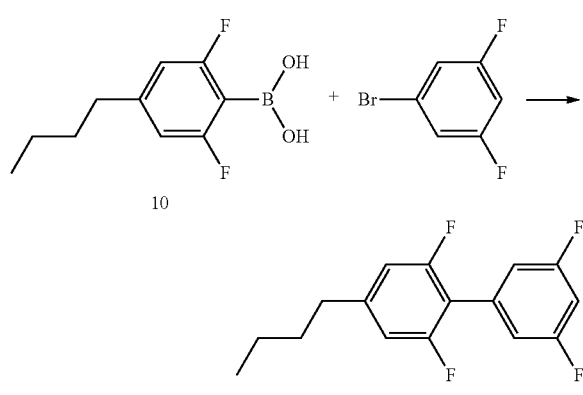

Step 2.2

57.2 g (150 mmol) disodiumtetraborate-decahydrate, 2.8 g (4 mmol) palladium chloride, 0.2 g (4 mmol) hydrazinium hydroxide, 39.4 g (0.2 mol) 1-bromo-3,5-difluorobenzene, 42.8 g (0.2 mol) 10 and 200 ml of water were combined. The mixture was heated to reflux for 6 h. After the usual workup 50 g (88%) of 11 was obtained.

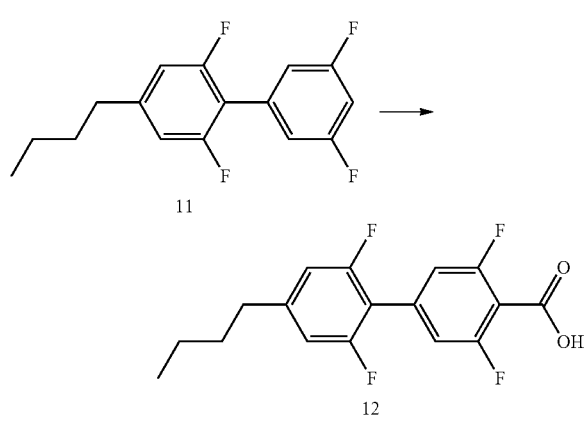

Step 2.3

50 g (175 mmol) 11 was dissolved in 300 ml tetrahydrofuran and cooled to −75° C. 118 ml (193 mmol) of 15% n-butyllithium in hexane was added dropwise below −70° C. and the mixture was stirred at that temperature for 1.5 h. The mixture was poured onto 500 g of solid carbon dioxide and allowed to warm to room temperature. After the usual workup 46.8 g (82%) of 12 was obtained as colorless crystals.

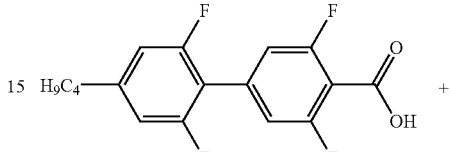

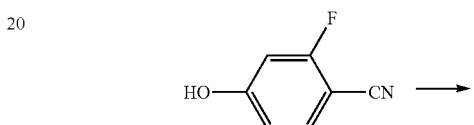

Step 2.4

16.3 g (50 mmol) 12, 8.5 g (55 mmol) 1-cyano-2,6-difluoro-4-hydroxy-benzene and 611 mg (5 mmol) 4-dimethylaminopyridine were combined with 200 ml dichloromethane and cooled to 0° C. Between 0 and 5° C. a solution of 11.3 g (55 mmol) N,N-dicyclohexylcarbodiimide in 50 ml dichloromethane was added dropwise. The mixture was then warmed to room temperature and stirred overnight. 1.4 g oxalic acid was added, and everything was stirred another 1.5 h. After the usual workup 20.5 g (88%) 13 (UUZU-4-N) was obtained.

$^1$H NMR (500 MHz, Chloroform-d) b 7.23-7.17 (m, 2H), 7.15-7.08 (m, 2H), 6.91-6.83 (m, 2H), 2.69-2.62 (m, 2H), 1.69-1.59 (m, 2H), 1.39 (h, J=7.4 Hz, 2H), 0.96 (t, J=7.4 Hz, 3H).

Phases: K 69 $N_f$ 92 N 93 I
Δn (20° C.): 0.16

Example 3: Synthesis of UUZU-5-N

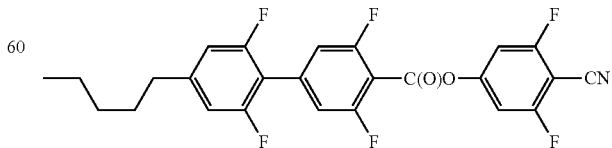

The compound is prepared in analogy to Example 2.
Melting point: 80° C.

Δn (20° C.): 0.16

In analogy to Examples 1 and 2 the following compounds are prepared: In the following table(s) the following abbreviations for the end groups are used

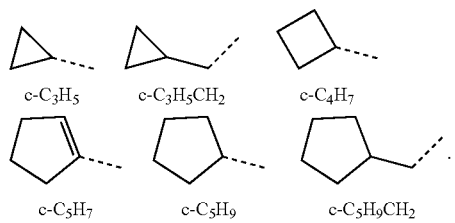

General Structure

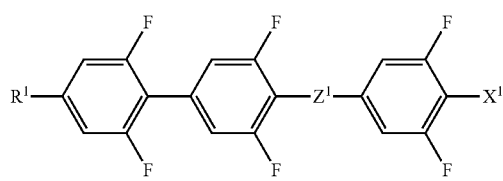

TABLE

Further compound examples

| Example no. | R¹ | Z¹ | X¹ | Melting point |
|---|---|---|---|---|
| 4. | H | COO | CN | |
| 5. | CH₃ | COO | CN | |
| 6. | C₂H₅ | COO | CN | 135° C. |
| 7. | n-C₃H₇ | COO | CN | 104° C. |
| 8. | C₂H₅CH(CH₃)CH₂ | COO | CN | |
| 9. | n-C₆H₁₃ | COO | CN | 60° C. |
| 10. | n-C₇H₁₅ | COO | CN | |
| 11. | n-C₃H₇CH(C₂H₅)CH₂ | COO | CN | |
| 12. | n-C₈H₁₇ | COO | CN | |
| 13. | c-C₃H₅ | COO | CN | |
| 14. | c-C₃H₅CH₂ | COO | CN | |
| 15. | c-C₄H₇ | COO | CN | |
| 16. | c-C₅H₇ | COO | CN | |
| 17. | c-C₅H₉ | COO | CN | |
| 18. | c-C₅H₉CH₂ | COO | CN | |
| 19. | CH₂=CH | COO | CN | |
| 20. | CH₃CH=CH | COO | CN | |
| 21. | CH₂=CH(CH₂)₂ | COO | CN | |
| 22. | CH₃O | COO | CN | |
| 23. | C₂H₅O | COO | CN | 104° C. |
| 24. | n-C₃H₇O | COO | CN | |
| 25. | n-C₄H₉O | COO | CN | |
| 26. | n-C₅H₁₁O | COO | CN | |
| 27. | H | CF₂O | CN | |
| 28. | CH₃ | CF₂O | CN | |
| 29. | C₂H₅ | CF₂O | CN | 84° C. |
| 30. | n-C₃H₇ | CF₂O | CN | 73° C. |
| 31. | n-C₅H₁₁ | CF₂O | CN | 39° C. |
| 32. | C₂H₅CH(CH₃)CH₂ | CF₂O | CN | |
| 33. | n-C₆H₁₃ | CF₂O | CN | 36° C. |
| 34. | n-C₇H₁₅ | CF₂O | CN | |
| 35. | n-C₃H₇CH(C₂H₅)CH₂ | CF₂O | CN | |
| 36. | n-C₈H₁₇ | CF₂O | CN | |
| 37. | c-C₃H₅ | CF₂O | CN | |
| 38. | c-C₃H₅CH₂ | CF₂O | CN | |
| 39. | c-C₄H₇ | CF₂O | CN | |
| 40. | c-C₅H₇ | CF₂O | CN | |
| 41. | c-C₅H₉ | CF₂O | CN | |
| 42. | c-C₅H₉CH₂ | CF₂O | CN | |
| 43. | CH₂=CH | CF₂O | CN | |
| 44. | CH₃CH=CH | CF₂O | CN | |
| 45. | CH₂=CH(CH₂)₂ | CF₂O | CN | |

TABLE-continued

Further compound examples

| Example no. | R¹ | Z¹ | X¹ | Melting point |
|---|---|---|---|---|
| 46. | CH₃O | CF₂O | CN | |
| 47. | C₂H₅O | CF₂O | CN | |
| 48. | n-C₃H₇O | CF₂O | CN | |
| 49. | n-C₄H₉O | CF₂O | CN | |
| 50. | n-C₅H₁₁O | CF₂O | CN | |

M. p.: Melting point.

MIXTURE EXAMPLES

Mixture Example 1

Liquid crystal media using the compounds according to the invention are prepared in the following.

The following mixtures are prepared and investigated.

Mixture M-1

Composition

| No. | Compound Abbreviation | Concentration/ % by weight | Physical properties |
|---|---|---|---|
| 1 | UUZU-4-N | 50.0 | T(N, I) = 94° C. |
| 2 | UUZU-5-N | 50.0 | |
| Σ | | 100.0 | |

Mixture M-1 shows a ferroelectric nematic phase from 77° C. to 31° C. (upon cooling).

Mixture Example 2

Mixture M-2

Composition

| No. | Compound Abbreviation | Concentration/ % by weight | Physical properties |
|---|---|---|---|
| 1 | UUQU-4-N | 60.0 | |
| 2 | UUQU-5-N | 40.0 | |
| Σ | | 100.0 | |

Mixture M-2 shows a ferroelectric nematic phase.

Mixture Example 3

| Mixture M-3 | | |
|---|---|---|
| Composition | | |
| Compound | | |
| No. | Abbreviation | % by weight | Physical properties |
| 1 | UUQU-4-N | 60.0 | |
| 2 | UUZU-4-N | 20.0 | |
| 3 | UUZU-5-N | 20.0 | |
| Σ | | 100.0 | |

Mixture M-3 shows a ferroelectric nematic phase.

Mixture Example 4

| Mixture M-4 | | | |
|---|---|---|---|
| Composition | | | |
| Compound | | Concentration/ | |
| No. | Abbreviation | % by weight | Physical properties |
| 1 | UUQU-4-N | 80.0 | |
| 2 | UUZU-4-N | 10.0 | |
| 3 | UUZU-5-N | 10.0 | |
| Σ | | 100.0 | |

Mixture M-4 shows a ferroelectric nematic phase.

Mixture Example 5

| Mixture M-5 | | | |
|---|---|---|---|
| Composition | | | |
| Compound | | Concentration/ | |
| No. | Abbreviation | % by weight | Physical properties |
| 1 | UUQU-2-N | 10.0 | T(N, I) = 42° C. |
| 2 | UUQU-3-N | 15.0 | |
| 3 | UUQU-4-N | 35.0 | |
| 4 | UUQU-5-N | 15.0 | |
| 5 | UUQU-6-N | 5.0 | |
| 6 | UUZU-4-N | 10.0 | |
| 7 | UUZU-5-N | 10.0 | |
| Σ | | 100.0 | |

Mixture M-5 shows a ferroelectric nematic phase below 38° C.

Mixture Example 6

| Mixture M-6 | | | |
|---|---|---|---|
| Composition | | | |
| Compound | | Concentration/ | |
| No. | Abbreviation | % by weight | Physical properties |
| 1 | UUQU-2-N | 10.0 | T(N, I) = 83° C. |
| 2 | UUQU-3-N | 12.0 | |
| 3 | UUQU-4-N | 17.0 | |
| 4 | UUZU-3-N | 6.0 | |
| 5 | UUZU-4-N | 14.0 | |
| 6 | UUZU-5-N | 6.0 | |
| 7 | GUZU-4-N | 8.0 | |
| 8 | GUUQU-3-N | 8.0 | |
| 9 | GUUQU-4-N | 12.0 | |
| 10 | DUUQU-4-N | 7.0 | |
| Σ | | 100.0 | |

Mixture M-6 shows a ferroelectric nematic phase below 73° C.

Further combinations of the embodiments of the current invention and variants of the invention are also disclosed by the claims.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever. The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of the formula I,

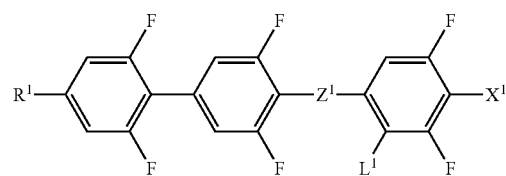

in which
$X^1$ denotes CN, F, $CF_3$, $OCF_3$, SCN, NCS, $SF_5$ or O—CF=$CF_2$,
$Z^1$ denotes -C(O)O—,
$L^1$ H or $CH_3$,
$R^1$ denotes an alkyl radical having 1 to 15 C atoms, where one or more $CH_2$ groups in these radicals are optionally replaced, independently of one another, by —C≡C—, —CH=CH—,

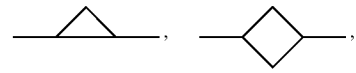

-continued

—O—, —S—, —CO—O— or

—O—CO— in such a way that O and S atoms are not linked directly to one another, and in which one or more H atoms are each optionally replaced by halogen, or denotes H.

2. A compound according to claim 1, wherein $R^1$ denotes alkyl having 1 to 8 carbon atoms, alkoxy with 1 to 8 carbon atoms, alkenyl with 2 to 8 carbon atoms, or alkenyloxy having 2 to 8 carbon atoms.

3. A compound according to claim 1, wherein $X^1$ denotes CN, F or $CF_3$.

4. A compound according to claim 1, wherein $R^1$ comprises 2 to 7 carbon atoms.

5. A compound according to claim 1 selected from compounds of the following formulae:

I-1

I-3

I-5

I-7

I-9

I-11

I-13

I-15

I-17

I-19

6. A compound according to claim 1, wherein $X^1$ denotes CN.

7. A compound according to claim 1, wherein $R^1$ denotes a straight-chain alkyl radical having 1 to 7 C atoms or an unbranched alkenyl radical having 2 to 8 C atoms.

8. A compound according to claim 1, wherein $R^1$ is a halogenated or unsubstituted alkyl radical having 1 to 15 C atoms, in which one or more $CH_2$ groups may be replaced, in each case independently of one another, by —C≡C— or —CH=CH—.

9. A compound according to claim 1 selected from compounds of the following formula:

I-A wherein $R^1$ is as defined in claim 1.

10. A liquid crystal medium comprising at least one compound of the formula I according to claim 1, wherein the medium is a ferroelectric nematic liquid crystal medium.

11. A liquid crystal medium comprising at least one compound of the formula I according to claim 1.

12. A liquid crystal medium according to claim 11, which comprises at least 20% by weight or more of one or more compounds of the formula I according to claim 1.

13. A process for preparation of a liquid crystal medium according to claim 11, comprising mixing at least one compound of the formula I with at least one further compound, and optionally adding additives.

14. A method of generating an electro-optical effect using a liquid crystal medium according to claim 11.

15. An electro-optical liquid-crystal display comprising a liquid crystal medium according to claim 12.

16. A process for the preparation of a liquid crystal medium according to claim 11, comprising mixing at least one compound of the formula I with at least one further mesogenic compound, and optionally adding additives.

17. A process for the preparation of a liquid crystal medium according to claim 11, comprising mixing at least one compound of the formula I with at least one further ferroelectric nematic compound, and optionally adding additives.

18. A compound according to the following formula:

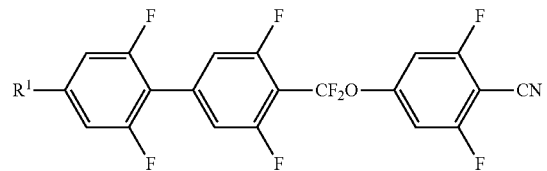

I-B wherein
R$^1$ is an alkyl radical having 1 to 15 C atoms, where one or more CH$_2$ groups in these radicals are optionally replaced, independently of one another, by —C≡C—, —CH=CH—,

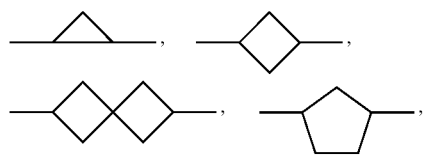

—O—, —S—, —CO—O— or —O—CO— in such a way that O and S atoms are not linked directly to one another, and in which one or more H atoms are each optionally replaced by halogen, or denotes H.

19. A liquid crystal medium comprising at least one compound of the formula I

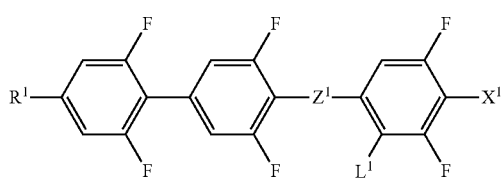

I in which
X$^1$ denotes CN,
Z$^1$ denotes —C(O)O— or —CF$_2$O—,
L$^1$ H or CH$_3$, and
R$^1$ denotes an alkyl radical having 1 to 15 C atoms, where one or more CH$_2$ groups in these radicals are optionally replaced, independently of one another, by —C≡C—, —CH=CH—,

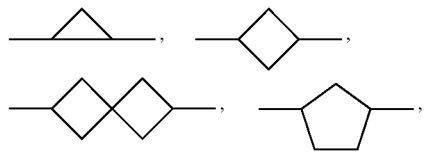

—O—, —S—, —CO—O— or
—O—CO— in such a way that O and S atoms are not linked directly to one another, and in which one or more H atoms are each optionally replaced by halogen, or denotes H.

20. The liquid crystal medium according to claim 19, wherein the medium is a ferroelectric nematic liquid crystal medium.

21. The liquid crystal medium according to claim 19, wherein the content of said at least one compound of the formula I is more than 40%.

22. A liquid crystal medium according to claim 21, wherein the content of said at least one compound of the formula I is more than 55%.

23. A liquid crystal medium according to claim 21, wherein said at least one compound of the formula I is selected from the following formulae:

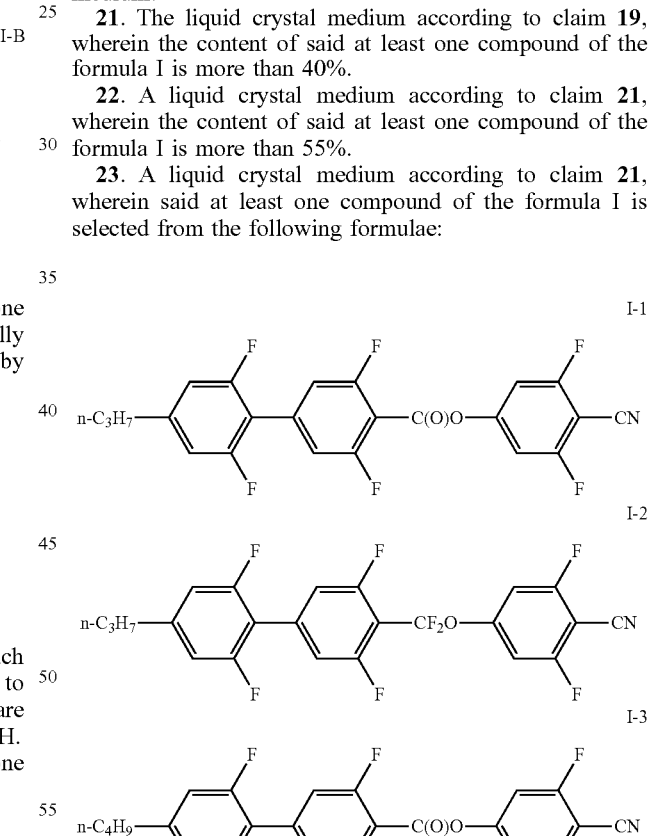

-continued
I-5
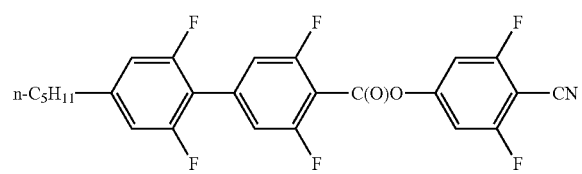
I-6
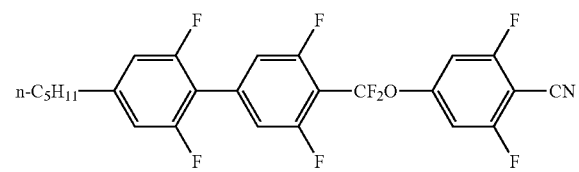
I-7
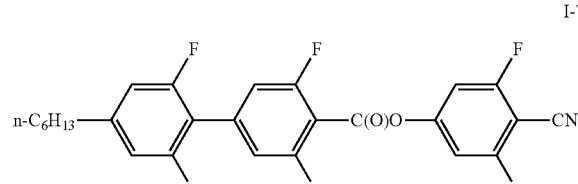
I-8
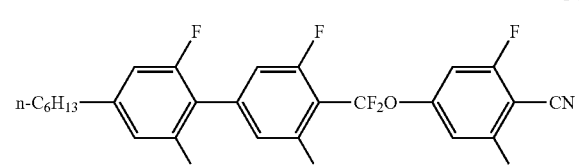
I-9
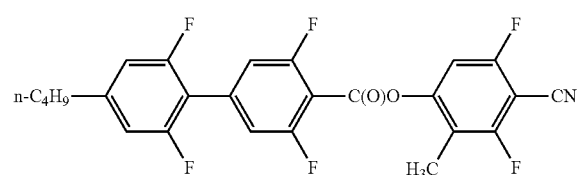
I-10
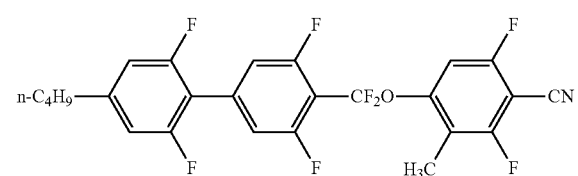
I-11
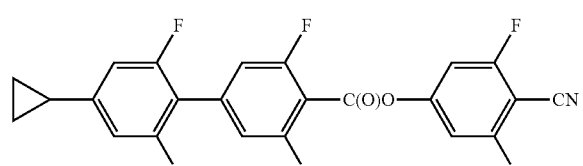
I-12
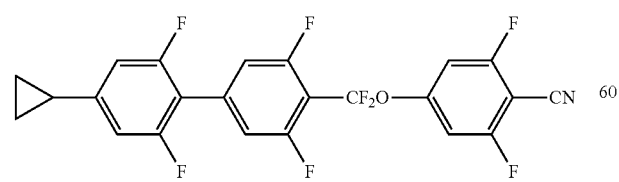
-continued
I-13
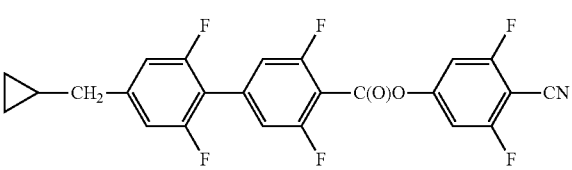
I-14
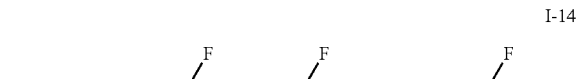
I-15
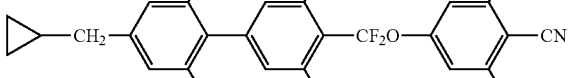
I-16
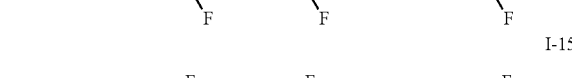
I-17
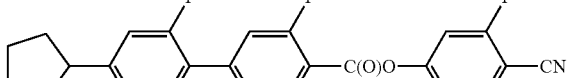
I-18
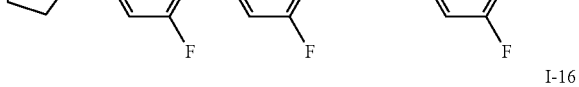
I-19
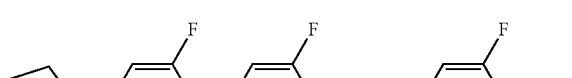
I-20
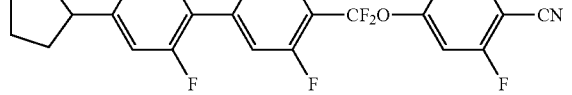
* * * * *